United States Patent [19]
Boyer et al.

[11] Patent Number: 4,916,711
[45] Date of Patent: Apr. 10, 1990

[54] LASING COMPOSITIONS AND METHODS FOR USING THE SAME

[76] Inventors: Joseph H. Boyer; Lee R. Morgan, both of 3839 Ulloa St., New Orleans, La. 70119

[21] Appl. No.: 251,188

[22] Filed: Sep. 29, 1988

[51] Int. Cl.$^4$ ............................................... H01S 3/20
[52] U.S. Cl. .................................... 372/53; 252/301.17
[58] Field of Search ............................. 372/53, 54, 39; 252/301.17

[56] References Cited

U.S. PATENT DOCUMENTS 4,774,339  9/1988  Haugland et al. .................. 548/405
4,799,230  1/1989  Pavalopoulos et al. ............. 372/53

OTHER PUBLICATIONS

Wories, H. J., "A Novel Water-Soluble Fluorescent Probe: Synthesis, Luminescence, and Biological Properties of the Sodium Salt of the 3,3', 5,5'-Tetramethyl-2,2'-Pyrromethene-1,1'-BF$_2$ Complex", *Recueil Des. Travaux Chemiques des Pays-Bas*, 104/11, Nov. 1985, pp. 288–291.

Primary Examiner—Leon Scott, Jr.
Attorney, Agent, or Firm—Klarquist, Sparkman, Campbell, Leigh & Whinston

[57] ABSTRACT

A new group of fluorescent organic materials having a variety of uses are described. They are especially useful as dye compounds in dye laser systems, and as photochemical agents in the treatment of diseased tissues using photodynamic therapy techniques. The materials involve a tri-cyclic compound having the following structure:

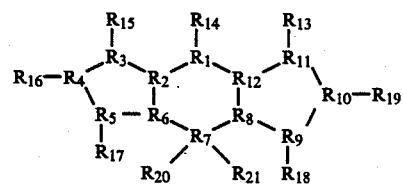

In this structure, $R_1$–$R_{21}$ represent a variety of organic and inorganic groups.

2 Claims, 2 Drawing Sheets

FIG.1

LASING COMPOSITIONS AND METHODS FOR USING THE SAME

This invention was made with government support under a grant from the State of Louisiana, and under Grant No. ONR(N00014-87-K-0254) awarded by the Department of the Navy, Office of the Chief of Naval Research. The U.S. Navy has certain rights in this invention.

The present invention generally relates to fluorescent chemical compositions, and more particularly to fluorescent chemical compounds suitable for use in a variety of medical, industrial, and scientific applications.

A demand currently exists for fluorescent chemical compounds having a high degree of stability and quantum fluorescence yield. These materials are usable for numerous purposes, including the generation of laser light. Substantial research has been conducted involving chemical laser systems capable of operating in the neat UV/visible/near IR spectral regions. Dye lasers offer the greatest promise in meeting these requirements. According to Maurer, A., *Lasers-Lightwave of the Future,* Arco Publishing Company, Inc., New York, 1982, liquid dye lasers were discovered in the early 60's. Initial experiments revealed that a "cell" or container of chemical dye used to block the mirror shutter of a ruby laser absorbed about 10% of the ruby laser's light and re-emitted it as coherent light having a distinctly different wavelength. This phenomenon was caused by the "Raman effect" in which the dye molecules scattered the light, with molecular vibrations in the dye causing emission of the light at a lower frequency compared to the incoming light frequency.

In the late 1960's, organic dye lasers tunable over a wide frequency range were developed. The light beams produced by these lasers were capable of being concentrated into an extremely narrow band through the use of defraction gradient systems or other optical devices.

Today, dye lasers are used for a variety of purposes in numerous technical fields including medicine and applied physics. For example, they may be used to conduct spectral analysis of chemical compounds. Also, they are useful in facilitating the analysis of photosynthetic and biomolecular reaction processes. Dye lasers in the medical field are used for numerous applications including cancer therapy, ophthalmological studies, and the like.

Typically, the lasing materials used in dye laser systems consist of fluorescent organic dye compounds dissolved in a liquid solvent. As discussed in Laurence, C. L., *The Laser Book*-A New Technology of Light, Prentice Hall Press, New York, 1986, one of the most important capabilities of dye lasers is their high degree of wavelength tunability. For example, the wavelength output of conventional dye lasers may be scanned over a 10-40 nm (nanometer) range. Through the use of different dye types, laser light output can be achieved at wavelengths from near ultraviolet to near infrared. According to Laurence, supra, dye lasers are readily tuned because the chemical dyes which they use have specific vibrational and rotational energy levels which are well characterized.

The selection of dyes for use in dye lasers is presently accomplished by trial and error. Numerous organic compounds showing strong fluorescence have been synthesized and are commercially available. However, very few of these materials are suitable for use in dye lasers. Currently used laser dyes primarily consist of coumarin and rhodamine compositions. These dyes, along with other commercially available materials, have only moderate energies and relatively high degrees of photodecomposition. In addition, currently available dyes require excitation using flashlamp systems with steep risetimes of 1 microsecond or less. Flashlamps meeting these requirements are difficult to construct for operation above 200 Joules.

Some of the problems associated with presently available laser dyes are related to the accumulation of dye molecules in a triplet state due to intersystem crossing. The triplet state molecules absorb laser light at a variable degree of efficiency, depending on the magnitude of triplet state absorption. Triplet-triplet (T-T) absorption is rather strong in most conventional laser dyes which are currently available.

The present invention involves improved laser dye compositions which are superior to previously used dyes in a variety of ways. Primarily, the dyes described herein have reduced T-T absorption and a lower laser action threshold. This enables the use of flashlamps with slower risetimes. These flashlamps have a longer functional life since they operate at lower driving voltages. Furthermore, a more efficient conversion of the flashlamp pump light due to reduced T-T absorption enables the production of a higher intensity laser beam. Finally, the dyes described herein have improved photochemical stability which results in reduced degradation of the dye materials.

Another important use of fluorescent dye compositions involves the detection and diagnosis of diseased tissues using photodynamic therapy (PDT) techniques. These techniques traditionally involve the administration of a photosensitizing drug to a patient, resulting in a distribution of the drug throughout the patient's body. The drug subsequently localizes in an area of diseased tissue which is then illuminated with light of an appropriate wavelength. This results in photochemical reactions in the diseased tissues which ultimately cause injury and/or death to the tissues.

Scientifically, there are to general mechanisms by which photosensitizing drugs are chemically altered upon illumination by an appropriate light source. The first mechanism (Type I) typically involves hydrogen atom abstraction from the drugs, thereby producing free radicals. Subsequent reactions of the radical products with other organic molecules or with oxygen results in biochemical destruction of the diseased tissue.

The other reaction mechanism (Type II) normally involves energy transfer from the electronically excited drugs to oxygen, producing singlet molecular oxygen which consequently reacts with a variety of substrates to produce oxygenated products. This pathway can also result in electron transfer from the excited drug to oxygen, producing an oxidized drug product in combination with superoxide ions. This reaction mechanism, along with the first mechanism described above is schematically presented in the following formula:

Photodynamic therapy has been used experimentally in cancer patients since 1972, with an estimated 3,000–4,000 patients treated throughout the world in the last six years. One experimental drug known as Photofrin II (a purified version of hematoporphyrin) is currently involved in randomized clinical trials. Other photosensitizing drugs used in photodynamic therapy procedures include phyhalocyanines (merocyanine 540), substituted purpurines, xanthenes (Rhodamine 123 6G&B) cationic cyanine dyes, chlorine polymers, chalcogenapyrylium dyes containing selenium or tellurium atoms in the chromophore, phenothiazinium derivatives, benzophenoxoniums (Nile Blue A) and triarylmethanes (Victoria Blue BO [VB-BO]). The exact mechanisms used by the above chemicals to destroy diseased tissues (including cancer cells) upon exposure to an excitory light source is currently unknown. Moreover, the efficacy of these and other currently used chemicals in photodynamic therapy has not been entirely substantiated, although positive results have been demonstrated in many instances.

Ongoing research has involved a search for photochemicals of improved stability which express minimal side effects. A major side effect caused by currently used drugs is the development of uncontrolled photosensitivity reactions in patients after systemic drug administration. Upon exposure to the sun, patients develop generalized skin photosensitization. Ongoing research has specifically involved a search for chemicals which avoid these side reactions.

As described above, numerous chemicals have been synthesized which show strong fluorescence and potential value as photosensitizing drugs. "Fluorescence" as used herein is defined as a spontaneous random emission of light resulting from an excited singlet state ($S_1$) of a molecule to the ground state ($S_0$) of the molecule. Many photochemical reactions arise from the triplet state ($T_1$). However, most photochemical drugs currently of interest experience adverse effects when the molecules accumulate in a triplet state due to intersystem crossing. These triplet molecules consequently absorb light more or less efficiently, depending on the magnitude of their triplet state absorption and concentration.

Thus, a need exists for photosensitizing chemicals which are useful in photodynamic therapy characterized by reduced triplet-triplet (T-T) absorption upon the application of light from an external source. Moreover, a need exists for photosensitizing drugs which are easily activated and are photochemically stable. The present invention satisfies this need, as described below.

SUMMARY OF THE INVENTION

It is an object of the present invention to provide new and improved organic fluorescent chemicals having a wide variety of uses.

It is another object of the invention to provide new and improved organic fluorescent chemicals which are suitable for use as laser dyes.

It is another object of the invention to provide new and improved laser dyes which offer a high degree of photochemical stability.

It is another object of the invention to provide new and improved laser dyes which are readily dissolved and easy to use.

It is another object of the invention to provide new and improved laser dyes which offer a high flourescence quantum efficiency ($Q_F > 0.7$).

It is another object of the invention to provide new and improved laser dyes with low triplet-triplet (T-T) absorption, thereby enabling the use of flashlamp pumping systems having slower risetimes.

It is another object of the invention to provide new and improved laser dyes which product laser light having a higher intensity in comparison with the light beams produced using conventional dyes.

It is another object of the invention to provide an improved method for photodynamic therapy.

It is another object of the invention to provide an improved photodynamic therapy method based on a new class of fluorescent photosenitizing chemicals.

It is yet another object of the invention to provide an improved photodynamic therapy method using fluorescent photosensitizing chemicals which are first introduced into the cancer tissues, followed by exposure of the tissues to light, thereby causing tissue destruction.

A still further object of the invention is to provide an improved photodynamic therapy method using fluorescent photosensitizing drugs which are readily soluble and easily prepared.

A still further object of the invention is to provide an improved photodynamic therapy method using fluorescent photosensitizing drugs which are highly stable.

An even further object of the invention is to provide an improved photodynamic therapy method using fluorescent photosensitizing drugs having reduced T-T absorption with a minimum overlap of fluorescence emission.

In accordance with the foregoing objects, a new group of fluorescent organic materials having a wide variety of uses is disclosed. The materials are especially useful as dye compounds in dye laser systems, and as photochemical agents in the treatment of diseased tissues using photodynamic therapy techniques. The materials described herein involve a substituted tri-cyclic compound having the following structure:

In the above structure, $R_1$–$R_{21}$ consist of a variety of selected organic and inorganic groups. The resulting compositions are highly fluorescent, photochemically stable, and exhibit low T-T absorption levels.

These and other objects, features, and advantages of the invention will be described below in the following detailed description of a preferred embodiment and accompanying examples.

DETAILED DESCRIPTION OF A PREFERRED EMBODIMENT

In accordance with the present invention, improved fluorescent chemical compositions are disclosed which have a variety of uses. As previously described, they are especially useful as dye media in laser systems, and as photochemical agents in photodynamic therapy techniques. In dye laser systems, the compounds described herein are superior to currently available dyes, including coumarin and rhodamine-based compositions in terms of power output, photostability, and solubility. When used in photodynamic therapy techniques, they are highly effective in destroying diseased tissues, including cancerous tumors and lesions.

The basic chemical tri-cyclic structure of the compositions described herein is as follows:

In this molecule, $R_1$–$R_{21}$ involve the following substituents:

$R_1$=C, N, B, Zn, Mg, or Cu
$R_2$=C or N
$R_3$=C or N
$R_4$=C, N, O or S
$R_5$=C or N
$R_6$=C or N
$R_7$=C, N, B, Zn, Mg, or Cu
$R_8$=C or N
$R_9$=C or N
$R_{10}$=C, N, O, or S
$R_{11}$=C or N
$R_{12}$=C or N
$R_{13}$–$R_{19}$=H, $C_nH_{2n+1}$ (n=1-3), phenyl, naphthyl, pyrryl, pyrazolyl, triazolyl, tetrazolyl, oxazolyl, isoxazoyl, thiazolyl, isothiazolyl, $C_nF_{2n+1}$ (n=1-3), ArF (Ar=phenyl or naphthyl), RCO (R=$C_nH_{2n+1}$; n=1-3), ($C_nF_{2n+1}$)CO (n=1-3), SO$_3$M (M=Na or K), CO$_2$H, CO$_2$M (M=Na or K), CO$_2$R (R=$C_nH_{2n+1}$; n=1-3), CO$_2$C$_n$F$_{2n+1}$ (n=1-3), cyclic alkyl groups having the formula $C_nH_{2n-1}$ (n=4-6), olefin derivatives having the formula $C_nH_{2n-1}$ (n=2-4), $C_nH_{2n-2}$ (n=2-4), $C_nH_{2n-m}$ (n=2-3; m=2-3), CONH$_2$, CONHR (R=$C_nH_{2n+1}$; n=1-3), CON(R)$_2$ (R=$C_nH_{2n+1}$; n=1-3), F, Cl, Br, I, CN, NC, NO$_2$, NO, ArN$_2$ (Ar=phenyl or naphthyl), NH$_2$, NHR (R=$C_nH_{2n+1}$; n=1-3), N(R)$_2$ (R=$C_nH_{2n+1}$; n=1-3), NHCOR (R=$C_nH_{2n+1}$; n=1-3), NHCOAr (Ar=phenyl, naphthyl), NCO, C(NOR)R (R=$C_nH_{2n+1}$; n=1-3), SO$_3$R (R=$C_nH_{2n+1}$; n=1-3), SO$_2$R (R=$C_nH_{2n+1}$; n=1-3), PO$_3$R (R=$C_nH_{2n+1}$; n=1-3), (CH$_2$)$_n$ Ar (n=1-3; Ar=phenyl, naphthyl), (CH$_2$)$_n$Het (n=1-3; Het=pyrryl, pyrazolyl, triazolyl, tetrazolyl, oxazolyl, isoxazolyl, thiazolyl, isothiazolyl) (CH$_2$)$_n$COR (R=$C_{n+}H_{2n+1}$; n=1-3), (CH$_2$)$_n$CO($C_nF_{2n+1}$) (n=1-3), (CH$_2$)$_n$SO$_3$M (n=1-3; M=Na or K), (CH$_2$)$_n$SO$_3$R (R=$C_nH_{2n+1}$; n=1-3), (CH$_2$)$_n$SO$_2$R (R=$C_nH_{2n+1}$; n=1-3); (CH$_2$)$_n$CO$_2$H (n=1-3), (CH$_2$)$_n$ CO$_2$R (R=$C_nH_{2n+1}$; n=1-3), (CH$_2$)$_n$F (n=1-3), (CH$_2$)$_n$Cl (n=1-3), (CH$_2$)$_n$ Br (n=1-3), (CH$_2$)$_n$ I (n=1-3), (CH$_2$)$_n$ CN (n=1-3), (CH$_2$)$_n$NC (n=1-3), (CH$_2$)$_n$NO$_2$ (n=1-3), (CH$_2$)$_n$NO (n=1-3), (CH$_2$)$_n$ArN$_2$ (n=1-3; Ar=phenyl, naphthyl), (CH$_2$)$_n$NH$_2$ (n=1-3); (CH$_2$)$_n$NHR (R=$C_nH_{2n+1}$; n=1-3), (CH$_2$)$_n$N(R)$_2$ (R=$C_nH_{2n+1}$; n=1-3), (CH$_2$)$_n$NHCOR (R=$C_nH_{2n+1}$; n=1-3), and (CH$_2$)$_n$NNCOAr (n=1-3; Ar=phenyl, naphthyl).
$R_{20}$=F, $C_nH_{2n+1}$ (n=1-3), phenyl, naphthyl, or H.
$R_{21}$=F, $C_nH_{2n+1}$ (n=1-3), phenyl, naphthyl, or H.

Preferred forms of the basic tri-cyclic compound described above are listed in the following examples:

EXAMPLE I

| | |
|---|---|
| $R_1$ = CH$_3$ | $R_{12}$ = CH$_3$ |
| $R_2$ = CH$_3$ | $R_{13}$ = CH$_3$ |
| $R_3$ = CH$_3$ | $R_{14}$ = CH$_3$ |
| $R_4$ = CH$_3$ | $R_{15}$ = CH$_3$ |
| $R_5$ = CH$_3$ | $R_{16}$ = H |
| $R_6$ = N | $R_{17}$ = CH$_3$ |
| $R_7$ = B | $R_{18}$ = CH$_3$ |
| $R_8$ = N | $R_{19}$ = H |
| $R_9$ = CH$_3$ | $R_{20}$ = F |
| $R_{10}$ = CH$_3$ | $R_{21}$ = F |
| $R_{11}$ = CH$_3$ | |

(4,4-difluoro-1,3,5,7,8-pentamethyl 4-bora-3a,4a-diaza-s-indacene)

To prepare this material, 2,4-dimethylpyrrole (2 g, 0.021 moles) was combined with freshly distilled acetyl chloride (18 ml) which was added drop-wise. This initial reaction and its intermediate product is shown as follows:

The above reaction was exothermic, and resulted in the production of a chemical mixture having a dark red color. The mixture was then heated under reflux for approximately 2.0 hours, followed by distillation and removal of excess acetyl chloride, The residue was treated with pentane, stirred for approximately 10 minutes at room temperature, and pentane was decanted. The residue was triturated with pentane (approximately 50 ml) for about 1.0 hours. A black, finely divided solid was removed, washed with approximately 10 ml of pentane, dried in air, and then dried in a desiccator under vacuum for about 2.0 hours. This material, which represents the intermediate product of the above reaction (pentamethylpyrromethene hydrochloride) weighed approximately 2.5 grams and had a melting point of 180°-182° C.

Next, the pentamethylpyrromethene hydrochloride (2.5 g. 0.01 moles) was dissolved in 350 ml of benzene. Triethyl amine (9.6 grams, 0.095 moles) was then added to the dissolved pentamethylpyrromethene hydrochloride, and the mixture stirred at room temperature for about 10 minutes. The reaction flask containing these materials was subsequently purged with nitrogen. Boron trifluoride etherate (16 ml, 0.13N) was added drop-wise over a period of 5 minutes. The mixture was heated under reflux for about 20 minutes, allowed to cool to room temperature, washed with three 100 ml portions of water, and dried over magnesium sulfate. The brownish-red solid product was purified by flash column chromatography over silica eluted with 60:40 benzene/pentane. This resulted in green-yellow fluorescent fractions which were subsequently combined and concentrated to a reddish-orange solid (2.1 grams). The solid recrystallized from ethyl acetate to give 1.7 g of product (4,4-difluoro-1,3,5,7,8-pentamethyl-4-bora-3a,-4a-diaza-s-indacene [$C_{14}H_{17}BF_2N_2$] m.p.=255°-257° C.). A schematic summary of the manufacturing steps used to produce the product from pentamethylpyrromethene hydrochloride is illustrated in the following reaction:

The foregoing procedure resulted in a 69% product yield. With respect to use of the product as a laser dye, it has a lasing threshold of 9.5 kV, with a lasing wavelength range of approximately 532–565 nm. This data was obtained using a 60 mg quantity of product dissolved in 250 ml of methanol in a 10 mm flashlamp D-1100 dye laser manufactured by the Phas-R Company of New Durham, New Hampshire (Model D-1100).

Figure 2:
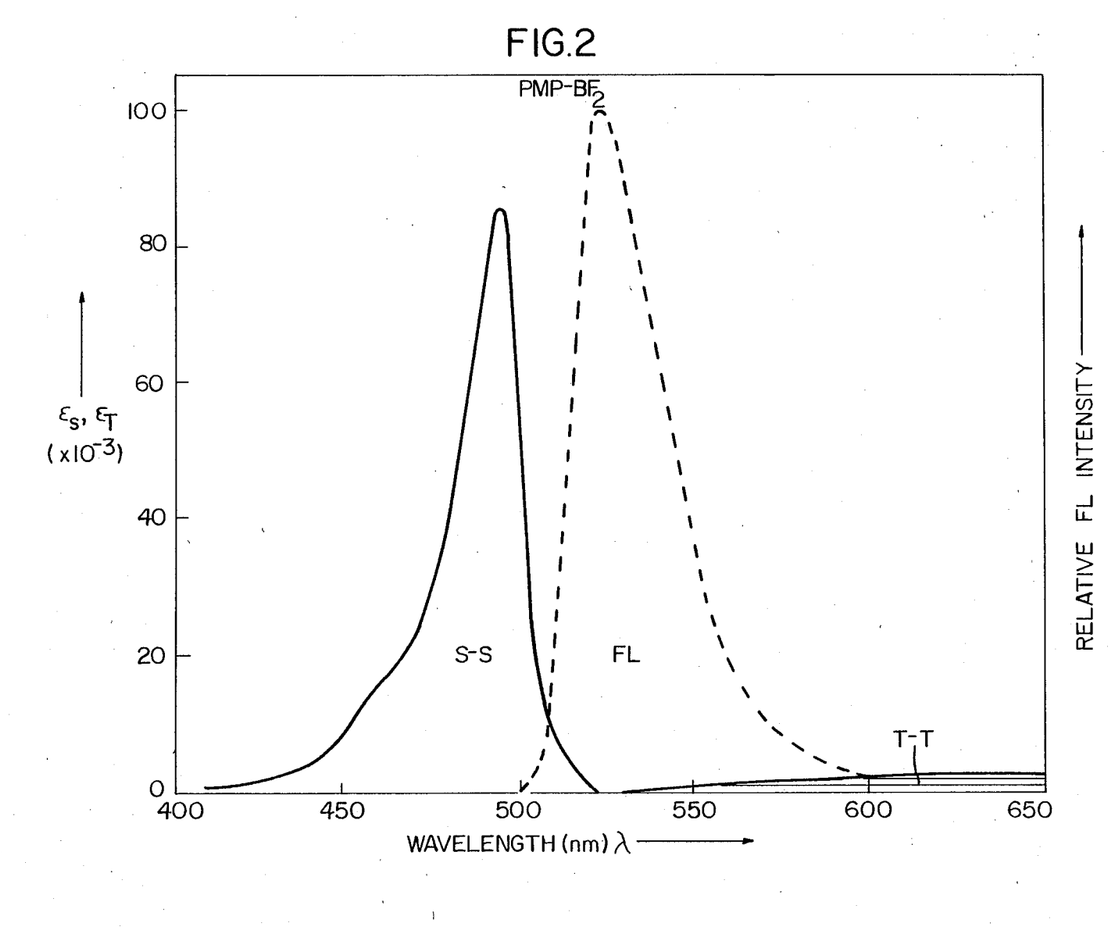
FIG. 2 is a graphical representation of the absorption and fluoroscence spectra of a preferred compound of the invention (4,4-difluoro-1,3,5,7,8-pentamethyl-4-bora-3a, 4a-diaza-s-indacene) dissolved in ethanol.

FIG. 2 shows the absorption (S-S) and fluorescence (FL) spectra of the compound of Example I (designated PMP-BF$_2$) dissolved in ethanol. The T-T absorption spectrum was recorded at 77K, employing a $1 \times 10^{-4}$ molar solution of 2-methyltetrahydrofuran as glassy solvent.

In addition, tests were conducted on the product in order to determine its solubility/fluorescence in various solvents. One property of the compositions described herein involves a variable degree of solubility/fluorescence relative to the solvents with which they are combined. Data showing a variety of different solvents combined with the product of Example I is presented below in Table I:

TABLE I

| Solvent | Solubility | Color of Solution | Fluorescence Room light | Fluorescence UV |
|---|---|---|---|---|
| CH$_2$Cl$_2$ | Soluble | yellowish green | yellowish green | yellowish green |
| CH$_3$CO$_2$C$_2$H$_5$ | partly soluble | brownish orange | yellowish green | yellowish green |
| O(CH$_2$CH$_2$)$_2$O | partly soluble | yellowish green | yellowish green | yellowish green |
| CH$_3$C≡N | partly soluble | yellowish green | yellowish green | yellowish green |
| C$_2$H$_5$OH(95%) | partly soluble | yellowish green | yellowish green | yellowish green |
| CF$_3$CH$_2$OH | partly soluble | green | yellowish green | yellowish green |
| (CF$_3$)$_2$CHOH | soluble | yellow | green | green |
| CClF$_2$—CFCl$_2$ | slightly soluble | yellow | green | green |
| H$_2$O | insoluble | — | — | — |

In addition, experiments were conducted in order to determine the photostability of the product of Example I. Basically, a solution was prepared by mixing 0.1 g of the product with 50 ml of dichloromethane solvent. The solution was placed in a 100 ml round bottom flask and irradiated with light from a sun lamp (250 watts at a distance of approximately 8 inches from the flask). No visual change in fluorescence was observed over a period of 22 days. However, another solution was made by combining 0.1 g of product in 250 ml of CH$_3$OH and 10 ml of CH$_2$Cl$_2$. Addition of the CH$_2$Cl$_2$ was undertaken to obtain complete dissolution. The solution was placed in a 250 ml round bottom flask and irradiated as described above. After 8 days, no fluorescence was observed. Thus, the use of different solvents will cause a variation in both the character and duration of fluorescence.

EXAMPLE II

| R$_1$ = CH$_3$ | R$_{12}$ = CH$_3$ |
| R$_2$ = CH$_3$ | R$_{13}$ = CH$_3$ |
| R$_3$ = CH$_3$ | R$_{14}$ = CH$_3$ |
| R$_4$ = CH$_3$ | R$_{15}$ = CH$_3$ |
| R$_5$ = CH$_3$ | R$_{16}$ = SO$_3$Na |
| R$_6$ = N | R$_{17}$ = CH$_3$ |
| R$_7$ = B | R$_{18}$ = CH$_3$ |
| R$_8$ = N | R$_{19}$ = SO$_3$Na |
| R$_9$ = CH$_3$ | R$_{20}$ = F |
| R$_{10}$ = CH$_3$ | R$_{21}$ = F |
| R$_{11}$ = CH$_3$ | |

(Disodium salt of 4,4-difluoro-1,3,5,7,8-pentamethyl-4-bora-3a,4a-diaza-s-indacene-2,6-disulfonic acid monohydrate)

To prepare this compound, 0.5 g (0.002 moles) of 4,4-difluoro-1,3,5,7,8-pentamethyl-4-bora-3a,4a-diaza-s-indacene (prepared as described above in Example I) were combined with 20 ml of methylene chloride. The mixture of these materials (maintained at −10° C.) was combined with a solution of chlorosulfonic acid (0.24 ml, 0.004 moles) added drop-wise using a syringe. The mixture was stirred at −10° C. for approximately 0.5 hours and allowed to reach room temperature over a period of 1 hour. A suspended yellow solid was isolated by filtration, dissolved in 75 ml water and the solution was neutralized with sodium bicarbonate (0.30 grams). Sodium bicarbonate was continuously added thereafter until effervescence stopped. The aqueous solution was concentrated to approximately one-quarter its previous volume. Upon the addition of about 15 ml of ethanol, a yellow precipitate appeared which was isolated and dried in a desiccator under vacuum. The precipitate weighed approximately 0.66 grams, had a melting point of about 260° C., and represented the final product (the sodium salt of 4,4-difluoro-1,3,5,7,8-pentamethyl-4-bora-3a,4a-diaza-s-indacene-2,6-disulfonic acid monohydrate-[$C_{14}H_{15}BF_2N_2O_6$ $S_2Na_2 \cdot H_2O$]). Production of this product is shown in the following basic reaction:

With respect to its use as a laser dye, the product had a lasing threshold of 10 kV with a lasing wavelength range of 545–585 nm. This data was obtained using a 60 mg quantity of product dissolved in 230 ml of $H_2O$ in a 10 mm flashlamp dye laser manufactured by the Phas-R Company (Model D-1100).

As in Example I, tests were conducted on the product in Example II in order to determine the fluorescence in various solvents. Data showing a variet of different solvent combined with the product of Example II is presented below in Table II:

TABLE II

| Solvent | Solubility | Color of Solution | Fluorescence Room light | UV |
|---|---|---|---|---|
| $CH_2Cl_2$ | Insoluble | | | |
| $CH_3CO_2C_2H_5$ | Insoluble | | | |
| $O(CH_2CH_2)_2O$ | Insoluble | | | |
| $CH_3C\equiv N$ | very slightly soluble | yellowish green | yellowish green | yellowish green |
| $C_2H_5OH(95\%)$ | very | yellowish | yellowish | yellowish |

TABLE II-continued

| Solvent | Solubility | Color of Solution | Fluorescence Room light | UV |
|---|---|---|---|---|
| | slightly soluble | green | green | green |
| $(CF_3)_2CHOH$ | Insoluble | | | |
| $H_2O$ | Soluble | reddish orange | yellowish green | yellowish green |

In addition, a further test was conducted in order to determine the photostability of the product. Specifically, 2.0 mg of the product in a 100 ml round bottom flask was dissolved in 50 ml of $H_2O$. The solution was then irradiated by light from a 250 watt sun lamp placed approximately 8 inches from the flask. UV spectral data was recorded periodically as shown below in Table III.

TABLE III

| TIME (h) | $\epsilon_{492}^{H_2O}$ |
|---|---|
| 0 | 76,995.38 |
| 0.5 | 76,755.22 |
| 1.0 | 75,556.52 |
| 1.5 | 76,755.52 |
| 2.5 | 75,316.35 |
| 3.5 | 73,757.26 |
| 6.0 | 69,799.55 |
| 20.0 | 52,049.62 |
| 21.5 | 51,569.90 |
| 23.5 | 46,173.05 |
| 25.5 | 45,573.40 |
| 28.0 | 41,016.06 |
| 30.5 | 37,178.46 |
| 44.0 | 20,388.19 |
| 50.0 | 13,192.355 |
| 52.5 | 599.653 |

In addition to the two compounds described above in Examples I and II, the following is another preferred compound:

EXAMPLE III $R_1 = CH_3$  $R_{12} = CH_3$
$R_2 = CH_3$  $R_{13} = CH_3$
$R_3 = CH_3$  $R_{14} = CH_2CH_3$
$R_4 = CH_3$  $R_{15} = CH_3$
$R_5 = CH_3$  $R_{16} = H$
$R_6 = N$  $R_{17} = CH_3$
$R_7 = B$  $R_{18} = CH_3$
$R_8 = N$  $R_{19} = H$
$R_9 = CH_3$  $R_{20} = F$
$R_{10} = CH_3$  $R_{21} = F$
$R_{11} = CH_3$ (4,4-difluoro-1,3,5,7-tetramethyl-8-ethyl-4-bora-3a,4a-diaza-s-indacene).

Table IV below summarizes the basic characteristics of the compounds of Examples I, II, and III in combination with a previously known compound (Rhodamine 590).

| | Laser Characteristics of Pyrromethene-$BF_2$ Complexes Under Flashlamp Excitation | | | |
|---|---|---|---|---|
| cpd. | Example I | Example II | Example III | Rhodamine 590 |
| $\lambda_L$ (nm) | 542 | 555 | 540 | 578 |
| $\Delta\lambda$ | 532–565 (33) | 545–585 (40) | 537–560 (23) | 565–612 (47) |
| Vth (kV) | 8–10 | 10 | 10 | 8 |
| $E_o$ (mJ) (V = 18 kV) | 85 | 80 | 90 | 100 |
| Life (kJ/L) | 50 (app.) | very long | * | 15 |

Laser Characteristics of Pyrromethene-BF$_2$ Complexes Under Flashlamp Excitation

| cpd. | Example I | Example II | Example III | Rhodamine 590 |
|---|---|---|---|---|
| Solvent | DMA/MeOH | DMA/MeOH | DMA/MeOH | DMA/MeOH |
| Conc (M) × 10$^4$ | 1.5 | 2 | 2 | 0.5 |

*After 1000 S at 25 J, $E_o$~80 mJ

Other specific compounds of interest include:

(s-Indacene) (1)

(3a,4a-Diaza-s-indacene) (2)

(4,8-Diaza-s-indacene) (3)

(3,7-Diaza-s-indacene) (4)

X = F, $C_nH_{2n+1}$, phenyl, naphthyl or H (4,4-Disubstituted-pyrromethene-B-complex) (5)

M = Zn, Mg or Cu (Pyrromethene-metal complex) (6)

(2,6-Dioxapyrromethene-BF$_2$ complex) (7)

(2,6-Dithia pyrromethene-BF$_2$ complex) (8)

Figure 1:
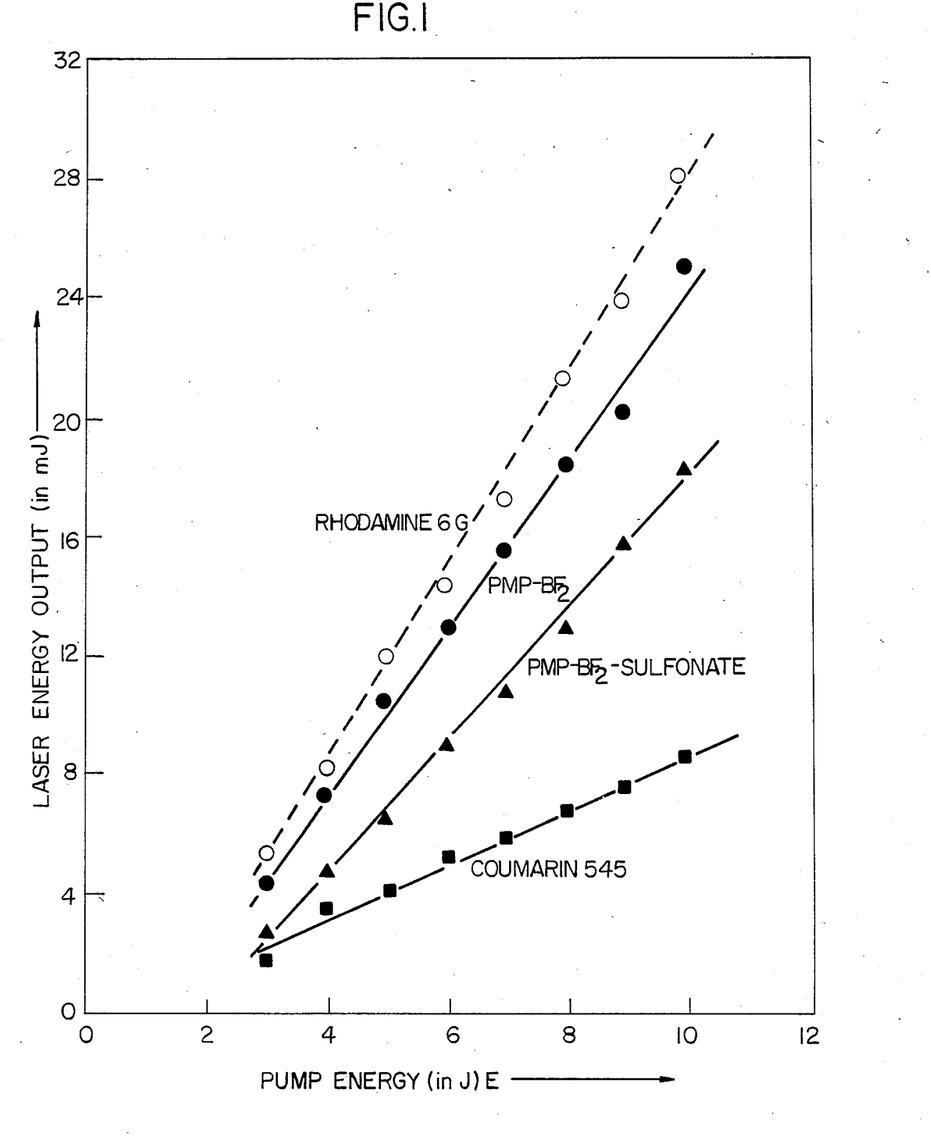
FIG. 1 is a graphical representation of laser energy output as a function of energy for preferred compounds of the invention (4,4-difluoro-1,3,5,7,8-pentamethyl-4-bora-3a, 4a-diaza-s-indacene and the disodium salt of 4,4-difluoro-1,3,5,7,8 pentamethyl-4-bora-3a,4a-diaza-s-indacene-2,6 disulfonic acid monohydrate) in comparison with previously known materials (Rhodamine 6G and Coumarin 545).

In addition, FIG. 1 shows the laser output E (in mJoule) as a function of input energy E (in Joule) of a 1.5×10$^{-4}$ molar solution of the compound of Example I (designated PMP-BF$_2$) dissolved in ethanol, a 2×10$^{-4}$ molar solution of Coumarin 545 dissolved in ethanol, a 2×10$^{-4}$ molar solution of Rhodamine 6G dissolved in ethanol, and a 2×10$^{-4}$ molar solution of the compound of Example II (designated PMP-BF$_2$-sulfonate) dissolved in ethanol.

USE OF THE COMPOSITIONS AS LASER DYES

As previously indicated, the compositions described herein function efficiently as laser dyes when used with conventional dyer laser systems. For example, an exemplary laser with which the compositions of the invention may be used includes a flashlamp-pumped dye laser system manufactured by the E.G. & G. Corporation (Model No. FX139C-2). This system has a flashlamp capable of producing pulses of approximately 200 ns risetime and 600 ns length at the half-width of the pulse. It is also capable of delivering 2 Joules at 6.32 kV, 5 Joules at 10.0 kV, and 10 Joules at 14.14 kV. The cell or containment vessel used in the system to retain the dye is about 2.5 mm in diameter and about 50 mm long.

As far as the solvents for the compounds are concerned, the data in Tables I and II is of importance. With respect to the compounds of Examples I and II, CH$_3$OH and H$_2$O respectively are preferred. In alternative systems, the compounds of the invention used as laser dyes may be in a gaseous form, or homogeneously dispersed in a polymer slug (e.g. a plastic such as methyl methacrylate).

Upon excitation, the compounds produce laser light having a high quantum fluorescence yield with low triplet-triplet (T-T) absorption, as well as a high degree of photostability. This improves the overall efficiency of the laser systems with which the dyes are used in comparison with previously used dye materials.

Use of The Compounds in Photodynamic Therapy

As indicated above, the compounds described herein are also of value as far as photodynamic therapy procedures are concerned. Testing has shown that administration of the materials, followed by excitation using an appropriate light source can result in the destruction of cancerous tumors and lesions.

Introduction of the compositions into the body of a subject is accomplished preferably by injection or topical application. Upon administration, the drugs spread throughout the body and into regions of diseased tissue (e.g. cancer tissue). Thereafter, the compositions are illuminated using light from a conventional light source (e.g. laser, sun lamp, etc.). In cases of cancer wherein the neoplastic growths are relatively near the skin surface, the light is applied directly through the skin. In other cases where neoplasms are deeper within the body (e.g. in the urinary bladder, gastrointestinal tract, respiratory tract, etc.) the light would be introduced by non-surgical or surgical entry into the body. For example, if the diseased tissue is in the respiratory tract, access could be accomplished by either surgical entry or non-surgical entry through the mouth using a fiber optic illumination system or the like.

Activation of the compounds by illumination with an appropriate light source results in photochemical processes which destroy diseased tissues. A specific example of this procedure is described with reference to breast cancer as follows:

In Vivo Test

Cancerous tumors were induced in fifty-day-old female Sprague Dawley rats by the oral feeding of 20 milligrams of dimethylbenzanthracene (DMBA) in 2 ml peanut oil. Tumors developed within six to eight weeks after feeding. After tumor development, an aqueous solution of the product of Example II described above (the disodium salt of 4,4-difluoro-1,3,5,7,8-pentamethyl-4-bora-3a,4a-diaza-s-indacene-2,6-disulfonic acid monohydrate) was injected into the rats. A 25 mg/ml of $H_2O$ solution was used. Thereafter, the rats were anesthetized using phenobarbital (2 mg/kg i.p.) and exposed from 10-30 minutes to light from either a 250 watt sum lamp or argon laser (488/514 nm and 628 nm). Tumor necrosis was observed within four days with greater than 75% tumor destruction. Normal tissue was not influenced. It is theorized that the compounds described herein, including the product of Example II reacts in a singlet state with tissue according to the first reaction mechanism (Type I) described above.

Having herein described a preferred embodiment of the invention, it is contemplated that suitable modifications may be made by those skilled in the art. For example, a variety of different compounds using the basic tri-cyclic structure presented herein may be used as laser dyes and/or photodynamic therapy agents. Thus, the invention shall only be construed in accordance with the following claims:

What is claimed is:

1. A method for producing laser light comprising the steps of:
   placing at least one lasing dye in a containment vessel, said dye comprising a compound of the formula wherein:
$R_1$ = C, N, B, Zn, Mg, or Cu
$R_2$ = C or N
$R_3$ = C or N
$R_4$ = C, N, O or S
$R_5$ = C or N
$R_6$ = C or N
$R_7$ = C, N, B, Zn, Mg, or Cu
$R_8$ = C or N
$R_9$ = C or N
$R_{10}$ = C, N, O, or S
$R_{11}$ = C or N
$R_{12}$ = C or N
$R_{13}$–$R_{19}$ = H, $C_nH_{2n+1}$ (n=1-3), phenyl, naphthyl, pyrryl, pyrazolyl, triazolyl, tetrazolyl, oxazolyl, isoxazolyl, thiazolyl, isothiazolyl, $C_nF_{2n+1}$ (n=1-3), ArF (Ar=phenyl or naphthyl), RCO (R=$C_nH_{2n+1}$; n=1-3), ($C_nF_{2n+1}$)CO (n=1-3), $SO_3M$ (M=Na or K), $CO_2H$, $CO_2M$ (M=Na or K), $CO_2R$ (R=$C_nH_{2n+1}$; n=1-3), $CO_2C_nF_{2n+1}$ (n=1-3), cyclic alkyl groups having the formula $C_nH_{2n-1}$ (n=4-6), olefin derivatives having the formula $C_nH_{2n-1}$ (n=2-4), $C_nH_{2n-2}$ (n=2-4), $C_nH_{2n-m}$ (n=2-3; m=2-3), $CONH_2$, CONHR (R=$C_nH_{2n+1}$; n=1-3), $CON(R)_2$ (R=$C_nH_{2n+1}$; n=1-3), F, Cl, Br, I, CN, NC, $NO_2$, NO, $ArN_2$ (Ar=phenyl or naphthyl), $NH_2$, NHR (R=$C_nH_{2n+1}$; n=1-3), $N(R)_2$ (R=$C_nH_{2n+1}$; n=1-3), NHCOR (R=$C_nH_{2n+1}$; n=1-3), NHCOAr (Ar=phenyl, naphthyl), NCO, C(NOR)R (R=$C_nH_{2n+1}$; n=1-3), $SO_3R$ (R=$C_nH_{2n+1}$; n=1-3), $SO_2R$ (R=$C_nH_{2n+1}$; n=1-3), $PO_3R$ (R=$C_nH_{2n+1}$; n=1-3), $(CH_2)_n$ Ar (n=1-3; Ar=phenyl, naphthyl, $(CH_2)_n$Het (n=1-3; Het=pyrryl, pyrazolyl, triazolyl, tetrazolyl, oxazolyl, isoxazolyl, thiazolyl, isothiazolyl), $(CH_2)_n$COR (R=$C_n+H_{2n+1}$; n=1-3), $(CH_2)_n$ CO($C_nF_{2n+1}$) (n=1-3), $(CH_2)_nSO_3M$ (n=1-3; M=Na or K), $(CH_2)_nSO_3R$ (R=$C_nH_{2n+1}$; n=1-3), $(CH_2)_nSO_2R$ (R=$C_nH_{2n+1}$; n=1-3); $(CH_2)_nCO_2H$ (n=1-3), $(CH_2)_n$ $CO_2R$ (R=$C_nH_{2n+1}$; n=1-3), $(CH_2)_nF$ (n=1-3), $(CH_2)_nCl$ (n=1-3), $(CH_2)_n$ Br (n=1-3), $(CH_2)_n$ I (n=1-3), $(CH_2)_n$ CN (n=1-3), $(CH_2)_n$NC (n=1-3), $(CH_2)_nNO_2$ (n=1-3), $(CH_2)_n$NO (n=1-3), $(CH_2)_nArN_2$ (n=1-3; Ar=phenyl, naphthyl), $(CH_2)_nNH_2$ (n=1-3), $(CH_2)_nNHR$ (R=$C_nH_{2n+1}$; n=1-3), $(CH_2)_nN(R)_2$ (R=$C_nH_{2n+1}$; n=1-3), $(CH_2)_nNHCOR$ (R=$C_nH_{2n+1}$; n=1-3), and $(CH_2)_nNHCOAr$ (n=1-3; Ar=phenyl, naphthyl),
$R_{20}$ = F, $C_nH_{2n+1}$ (n=1-3), phenyl, naphthyl, or H,
$R_{21}$ = F, $C_nH_{2n+1}$ (n=1-3), phenyl, naphthyl, or H; and electronically exciting said dye in said vessel in order to produce said laser light.

2. A method for producing a laser light comprising the steps of:
   placing at least one lasting dye in a containment vessel, said dye comprising a compound having a formula selected from the group consisting of:

-continued and

-continued and electronically exciting said solution in said vessel in order to produce said laser light.

* * * * *